US006984509B1

(12) United States Patent
Mao et al.

(10) Patent No.: US 6,984,509 B1
(45) Date of Patent: Jan. 10, 2006

(54) STEROID DEHYDROGENASE 34 AND THE POLYNUCLEOTIDE ENCODING SAME

(75) Inventors: Yumin Mao, Shanghai (CN); Yi Xie, Shanghai (CN)

(73) Assignee: Shanghai Bio Road Gene Development, Ltd., Shanghai (CN)

( * ) Notice: Subject to any disclaimer, the term of this patent is extended or adjusted under 35 U.S.C. 154(b) by 424 days.

(21) Appl. No.: 10/111,105

(22) PCT Filed: Oct. 16, 2000

(86) PCT No.: PCT/CN00/00327

§ 371 (c)(1),
(2), (4) Date: Apr. 22, 2002

(87) PCT Pub. No.: WO01/31026

PCT Pub. Date: May 3, 2001

(30) Foreign Application Priority Data

Oct. 22, 1999  (CN) ................ 99119815 A

(51) Int. Cl.
*C12N 9/04* (2006.01)
*C12N 1/20* (2006.01)
*C12N 15/00* (2006.01)
*C12P 21/04* (2006.01)
*C07H 21/04* (2006.01)

(52) U.S. Cl. ............... 435/190; 435/4; 435/6; 435/69.7; 435/71.1; 435/252.3; 435/320.1; 435/440; 536/23.2; 536/23.5

(58) Field of Classification Search ............... 435/190, 435/252.3, 320.1, 71.1, 440, 6, 252, 4, 69.7; 536/23.2, 23.5
See application file for complete search history.

(56) References Cited

FOREIGN PATENT DOCUMENTS

| JP | 4-365475 | 12/1992 |
|---|---|---|
| WO | 97/11162 | 3/1997 |
| WO | 97/20942 | 6/1997 |

OTHER PUBLICATIONS

Geissler et al. NCBI database—U05659—1994.*

* cited by examiner

*Primary Examiner*—Manjunath Rao
*Assistant Examiner*—Yong Pak
(74) *Attorney, Agent, or Firm*—Crowell & Moring LLP

(57) ABSTRACT

The present invention discloses a novel polypeptide, a steroid dehydrogenase 34, the polynucleotide encoding the polypeptide and the method for producing the polypetide by DNA recombinant technology. The invention also discloses the uses of the polypeptide in methods for tresting various diseases, such as steroid hormone dysbolismus disease, such as sex dysgenopathy, some endocrine and metabolic syndrome, viarous tumors of human reproductive system, bile acid dysbolismus, etc. The invention also discloses the agonists against the polypeptide and the therapeutic action thereof. The invention also discloses the uses of the polynucleotide encoding the novel steroid dehydrogenase 34.

8 Claims, 2 Drawing Sheets

```
                Identity=99/252    (39%),    Similarity=151/252  (59%)

Steroid                :42  IQYGRWAVVSGATDGIGKAYAEELASRGLNIILISRNEEKLQVVAKDIADTYKVETDII  101
dehydrogenase 34
                            G+WAV++GA DGIGKAY+ ELA RGLN++LISR EKL+ +A +I  T        II
17 beta-hydroxy-steroid
dehydrogenase (type 3) :44  LRSMGQWAVITGAGDGIGKAYSFELAKRGLNVVLISRTLEKLEAIATEIERTTGRSVKII  103

Steroid                :102 VADFSSGREIYLPIREALKDKDVGILVNNVGVFYP--YPQYFTQLSEDKLWDIINVNIAA  159
dehydrogenase 34
                            ADF+    +IY  I+E L   ++GILVNNVG+  P         + D++  +I+ NI +
17 beta-hydroxy-steroid:104 QADFTKD-DIYEHIKEKLAGLEIGILVNNVGML-PNLLPSHFLN-APDEIQSLIHCNITS 160
dehydrogenase (type 3)

Steroid                :160 ASLMVHVVLPGMVERKKGAIVTISSGSCCKPTPQLAAFSASKAYLDHFSRALQYEYASKG 219
dehydrogenase 34
                            M  ++L  M  R+KG I+ ISSG     P P +  +SASKA++     FS+ALQ EY +K
17 beta-hydroxy-steroid:161 VVKMTQLILIGHMESRQKGLILNISSGIALFPWPLYSMYSASKAFVCAPSKALQEEYKAKE 220
dehydrogenase (type 3)

Steroid                :220 IFVQSLIPFYVATSMTAPSNFLHRCSWLVPSPKVYAHHAVSTLGISKRTTGYWSHSIQFL 279
dehydrogenase 34
                            +  +Q L P+ V+T+MT    +L+ + +  +  +++ +   I  TG  +H I
17 beta-hydroxy-steroid:221 VIIQVLTPYAVSTAMT---KYLNT-NVITKTADEFVKESLNYVTIGGETCGCLAHEILAG 276
dehydrogenase (type 3)

Steroid                :280 FAQYMPEWLWVWGA 293 (SEQ ID NO: 2)
dehydrogenase 34
                            F   +P W +  GA
17 beta-hydroxy-steroid:277 FLSLIPAWAFYSGA 290 (SEQ ID NO: 8)
dehydrogenase (type 3)
```

Identity=99/252    (39%),    Similarity=151/252  (59%)

Steroid dehydrogenase 34 :42 IQYGRWAVVSGATDGIGKAYAEELASRGLNIILISRNEEKLQVVAKDIADTYKVETDII 101

G+WAV++GA DGIGKAY+ ELA RGLN++LISR  EKL+ +A +I T         II 17 beta-hydroxy-steroid dehydrogenase (type 3) :44 LRSMGQWAVITGAGDGIGKAYSFELAKRGLNVVLISRTLEKLEAIATEIERTTGRSVKII 103

Steroid dehydrogenase 34 :102 VADFSSGREIYLPIREALKDKDVGILVNNVGVFYP--YPQYFTQLSEDKLWDIINVNIAA 159

ADF+    +IY I+E L  ++GILVNNVG+  P         + D++   +I+ NI +

17 beta-hydroxy-steroid dehydrogenase (type 3) :104 QADFTKD-DIYEHIKEKLAGLEIGILVNNVGML-PNLLPSHFLN-APDEIQSLIHCNITS 160

Steroid dehydrogenase 34 :160 ASLMVHVVLPGMVERKKGAIVTISSGSCCKPTPQLAAFSASKAYLDHFSRALQYEYASKG 219

M  ++L  M  R+KG I+ ISSG      P P  + +SASKA++   FS+ALQ EY +K 17 beta-hydroxy-steroid dehydrogenase (type 3) :161 VVKMTQLILKHMESRQKGLILNISSGIALFPWPLYSMYSASKAFVCAFSKALQEEYKAKE 220

Steroid dehydrogenase 34 :220 IFVQSLIPFYVATSMTAPSNFLHRCSWLVPSPKVYAHHAVSTLGISKRTTGYWSHSIQFL 279

+ +Q L P+ V+T+MT   +L+ + +    +   +++ +  I   TG  +H I 17 beta-hydroxy-steroid dehydrogenase (type 3) :221 VIIQVLTPYAVSTAMT---KYLNT-NVITKTADEFVKESLNYVTIGGETCGCLAHEILAG 276

Steroid dehydrogenase 34 :280 FAQYMPEWLWVWGA 293 (SEQ ID NO: 2)

F    +P W +  GA 17 beta-hydroxy-steroid dehydrogenase (type 3) :277 FLSLIPAWAFYSGA 290 (SEQ ID NO: 8)

Figure 1

STEROID DEHYDROGENASE 34 AND THE
POLYNUCLEOTIDE ENCODING SAME

FIELD OF INVENTION

The invention relates to the field of biotechnology. In particular, the invention relates to a novel polypeptide—a steroid dehydrogenase 34, and a polynucleotide sequence encoding said polypeptide. The invention also relates to the method for the preparation and application of said polynucleotide and polypeptide.

TECHNICAL BACKGROUND

A member of short-chain dehydrogenase/reductase family (sdr) is 17beta-hydroxy-steroid dehydrogenase (type VI), consisting of 309 amino acid residues, and containing a common characteristic conserved sequence of the sdr family. It has 39% homology at the amino acid level with another member of the family, 17beta-hydroxy-steroid dehydrogenas, (type III).

The enzyme 17beta-hydroxy-steroid dehydrogenase catalyzes the dehydrogenation/reduction of a special 17beta-hydroxy-steroid hormone or prohormone. The product can be used as a hormone to act directly or as a prohormone to be farther used by other enzymes. 17beta-hydroxy-steroid dehydrogenase (type I) reduces estrogen and androgen; 17beta-hydroxy-steroid dehydrogenase (type II) catalyzes the interconverter between testosterone and androstenedione and the interconversion between estradiol and estrone; 17beta-hydroxy-steroid dehydrogenase (type III) catalyzes redox reaction of androstenedione, testosterone and dihydrotestestosterone; 17beta-hydroxy-steroid dehydrogenase (type IV) catalyzes the interconversion between estradiol and estrone.

It is proved that 17beta-hydroxy-steroid dehydrogenase has numerous biological functions. Mutations in the 17beta-hydroxy-steroid dehydrogenase (type II) gene are possible causes of hereditary mammary-ovarian cancer. The enzyme plays an important role in the carcinogenesis of mammary gland and ovary in human. 17beta-hydroxy-steroid dehydrogenase (type III) plays an important role in the development of male sexuality. If this enzyme is in a low level resulted from genetic mutation, it may cause male pseudohermaphroditism and gynecomasty; 17beta-hydroxy-steroid dehydrogenase (type IV) plays an important role in catalyzing the oxidation of the precursor of bile acid. The common function of this hydroxy-steroid dehydrogenase family is to catalyze metabolism of steroid. Its product as a hormone binds with the receptor more efficiently than the prohormone thereby effecting functional rgulations. The product can also be used by other enzymes as a prohormone, thus continuing the pathway of steroid metabolism.

OBJECTIVES OF THE INVENTION

One objective of the invention is to provide an isolated novel polypeptide, i.e., a steroid dehydrogenase 34, and fragments, analogues and derivatives thereof.

Another objective of the invention is to provide a polynucleotide encoding said polypeptide.

Another objective of the invention is to provide a recombinant vector containing a polynucleotide encoding a steroid dehydrogenase 34.

Another objective of the invention is to provide a genetically engineered host cell containing a polynucleotide encoding a steroid dehydrogenase 34.

Another objective of the invention is to provide a method for producing a steroid dehydrogenase 34.

Another objective of the invention is to provide an antibody against a steroid dehydrogenase 34.

Another objective of the invention is to provide mimetics, antagonists, agonists, and inhibitors for the polypeptide of the a steroid dehydrogenase 34.

Another objecitve of the invention is to provide a method for the diagnosis and treatment of the diseases associated with an abnormality of a steroid dehydrogenase 34.

SUMMARY OF THE INVENTION

In the first aspect, the invention provides a novel isolated steroid dehydrogenase 34 which is originated from human and comprises a polypeptide having the amino acid sequence of SEQ ID NO: 2, or its conservative mutants, or its active fragments, or its active derivatives and its analogues. Preferably, the polypeptide is a polypeptide having the amino acid sequence of SEQ ID NO: 2.

In the second aspect, the invention provides an isolated polynucleotide encoding said polypeptide, the polynucleotide comprises a nucleotide sequence that shares at least 70% homology to the nucleotide sequence selected from the group consisting of (a) the polynucleotide encoding said a steroid dehydrogenase 34; and (b) a polynucleotide complementary to the polynucleotide (a). Preferably, said nucleotide sequence encodes a polypeptide comprising the amino acid sequence of SEQ ID NO: 2. More preferably, said nucleotide sequence is selected from the group consisting of (a) the sequence of position 112–1041 in SEQ ID NO: 1; and (b) the sequence of position 1–1416 in SEQ ID NO: 1.

In the third aspect, the invention provides a vector comprising said polynucleotide and a host cell transformed or transfected by said vector or directly transformed or transfected by said polynucleotide.

Other aspects of the invention are apparent to the skilled in the art in view of the disclosure.

BRIEF DESCRIPTION OF THE DRAWINGS

The following drawings are provided to illustrate the embodiment of the invention, not to limit the scope of invention defined by the claims.

FIG. 1 shows an alignment comparison of amino acid sequences of a steroid dehydrogenase 34 of the invention (SEQ ID NO: 2) and 17beta-hydroxy-steroid dehydrogenase, (type III) (SEQ ID NO: 8). The upper sequence is a steroid dehydrogenase 34, and the lower sequence is 17beta-hydroxy-steroid dehydrogenase, (type III). The identical and similar amino acids are indicated by a one-letter code of amino acid and "+" respectively.

DETAILED DESCRIPTION OF THE INVENTION

Figure 2:
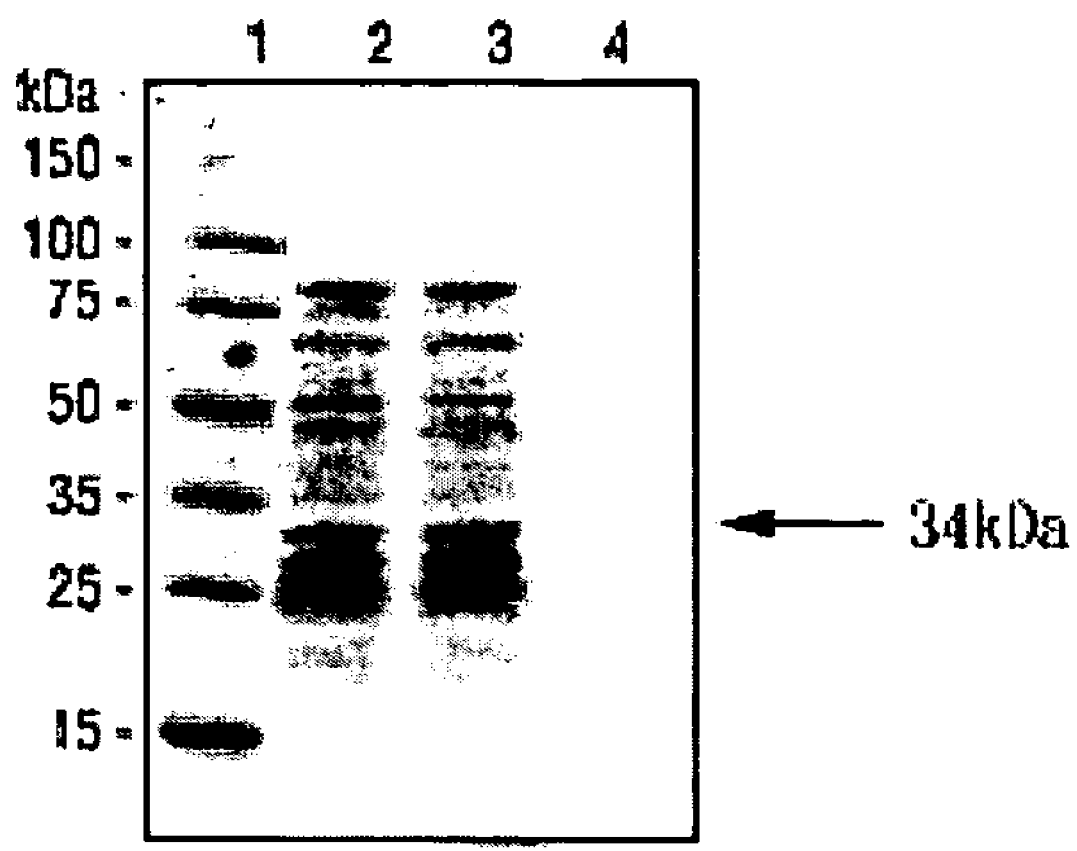
FIG. 2 shows the SDS-PAGE of the isolated a steroid dehydrogenase 34, which has a molecular weight of 34.0 kDa. The isolated protein band is marked with an arrow.

As used herein, the term "isolated" refers to a substance which has been isolated from the original environment. For naturally occurring substance, the original environment is the natural environment. For example, the polynucleotide and polypeptide in a naturally occurring state in the viable cells are not isolated or purified. However, if the same polynucleotide and polypeptide have been isolated from other components naturally accompanying them, they are isolated or purified.

As used herein, "isolated a steroid dehydrogenase 34" means that a steroid dehydrogenase 34 does not essentially contain other proteins, lipids, carbohydrate or any other substances associated therewith in nature. The skilled in the art can purify a steroid dehydrogenase 34 by standard protein purification techniques. Essentially the purified polypeptide forms a single main band on a non-reductive PAGE gel. The purity of a steroid dehydrogenase 34 polypeptide can be analyzed by amino acid sequence analysis.

The invention provides a novel polypeptide—a steroid dehydrogenase 34, which the amino acid sequence shown in SEQ ID NO: 2. The polypeptide of the invention may be a recombinant polypeptide, natural polypeptide, or synthetic polypeptide, preferably a recombinant polypeptide. The polypeptide of the invention may be a purified natural product or a chemically synthetic product. Alternatively, it may be produced from prokaryotic or eukaryotic hosts, such as bacteria, yeast, higher plant, insect, and mammal cells, using recombinant techniques. Depending on the host used in the protocol of recombinant production, the polypeptide of the invention may be glycosylated or non-glycosylated. The polypeptide of the invention may or may not comprise the starting Met residue.

The invention further comprises fragments, derivatives and analogues of a steroid dehydrogenase 34. As used in the invention, the terms "fragment", "derivative" and "analogue" mean the polypeptide that essentially retains the same biological functions or activity of A steroid dehydrogenase 34 of the invention. The fragment, derivative or analogue of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues are substituted with other residues, include a substituent group; or (iii) one in which the mature polypeptide is fused with another compound, such as a compound to increase the half-life of the polypeptide (for example, polyethylene glycol); or (iv) one in which additional amino acids are fused to the mature polypeptide, such as a leader or secretory sequence or a sequence which is employed for purification of the mature polypeptide or a proprotein sequence. Such fragments, derivatives and analogs are deemed to be within the scope of the skilled in the art from the teachings herein.

The invention provides an isolated nucleic acid or polynucleotide which comprises the polynucleotide encoding an amino acid sequence of SEQ ID NO: 2. The polynucleotide sequence of the invention includes the nucleotide sequence of SEQ ID NO: 1. The polynucleotide of the invention was identified in a human embryonic brain cDNA library. Preferably, it comprises a full-length polynucleotide sequence of 1461 bp, whose ORF (112–1041) encodes 309 amino acids. Based on amino acid homology comparison, the encoded polypeptide is 45% homologous to 17beta-hydroxy-steroid dehydrogenase, (type III). Further, this polypeptide contains conservative bases of short strand dehydrogenase/reductase gene family. This novel human a steroid dehydrogenase 34 has similar structures and biological functions to those of 17beta-hydroxy-steroid dehydrogenas, (type III).

The polynucleotide according to the invention may be in the forms of DNA or RNA. The forms of DNA include cDNA, genomic DNA, and synthetic DNA, etc., in single stranded or double stranded form. DNA may be an encoding strand or non-encoding strand. The coding sequence for mature polypeptide may be identical to the coding sequence shown in SEQ ID NO: 1, or is a degenerate sequence. As used herein, the term "degenerate sequence" means an sequence which encodes a protein or peptide comprising a sequence of SEQ ID NO: 2 and which has a nucleotide sequence different from the sequence of coding region in SEQ ID NO: 1.

The polynucleotide encoding the mature polypeptide of SEQ ID NO: 2 include those encoding only the mature polypeptide, those encoding mature polypeptide plus various additional coding sequence, the coding sequence for mature polypeptide (and optional additional coding sequence) plus the non-coding sequence.

The term "polynucleotide encoding the polypeptide" includes polynucleotides encoding said polypeptide and polynucleotides comprising additional coding and/or non-coding sequences.

The invention further relates to variants of the above polynucleotides which encode a polypeptide having the same amino acid sequence of invention, or a fragment, analogue and derivative of said polypeptide. The variant of the polynucleotide may be a naturally occurring allelic variant or a non-naturally occurring variant. Such nucleotide variants include substitution, deletion, and insertion variants. As known in the art, an allelic variant may be a substitution, deletion, and insertion of one or more nucleotides without substantially changing the functions of the encoded polypeptide.

The present invention further relates to polynucleotides, which hybridize to the hereinabove-described sequences, that is, there is at least 50% and preferably at least 70% identity between the sequences. The present invention particularly relates to polynucleotides, which hybridize to the polynucleotides of the invention under stringent conditions. As herein used, the term "stringent conditions" means the following conditions: (1) hybridization and washing under low ionic strength and high temperature, such as 0.2×SSC, 0.1% SDS, 60° C.; or (2) hybridization after adding denaturants, such as 50% (v/v) formamide, 0.1% bovine serum/ 0.1% Ficoll, 42° C.; or (3) hybridization only when the homology of two sequences at least 95%, preferably 97%. Further, the polynucleotides which hybridize to the hereinabove described polynucleotides encode a polypeptide which retains the same biological function and activity as the mature polypeptide of SEQ ID NO: 2.

The invention also relates to nucleic acid fragments hybridized with the hereinabove sequence. As used in the present invention, the length of the "nucleic acid fragment" is at least more than 10 bp, preferably at least 20–30 bp, more preferably at least 50–60 bp, and most preferably at least 100 bp. The nucleic acid fragment can be used in the amplification techniques of nucleic acid, such as PCR, so as to determine and/or isolate the polynucleotide encoding a steroid dehydrogenase 34.

The polypeptide and polynucleotide of the invention are preferably in the isolated form, preferably purified to be homogenous.

According to the invention, the specific nucleic acid sequence encoding a steroid dehydrogenase 34 can be obtained in various ways. For example, the polynucleotide is isolated by hybridization techniques well-known in the art, which include, but are not limited to 1) the hybridization between a probe and genomic or cDNA library so as to select a homologous polynucleotide sequence, and 2) antibody screening of expression library so as to obtain polynucleotide fragments encoding polypeptides having common structural features.

According to the invention, DNA fragment sequences may further be obtained by the following methods: 1) isolating double-stranded DNA sequence from genomic DNA; and 2) chemical synthesis of DNA sequence so as to obtain the double-stranded DNA.

Among the above methods, the isolation of genomic DNA is least frequently used. A commonly used method is the direct chemical synthesis of DNA sequence. A more frequently used method is the isolation of cDNA sequence. A standard method for isolating the cDNA of interest is to isolate mRNA from donor cells that highly express said gene followed by reverse transcription of mRNA to form plasmid or phage cDNA library. There are many established techniques for extracting mRNA and the kits are commercially available (e.g. Qiagene). Conventional method can be used to construct cDNA library (Sambrook, et al., Molecular Cloning, A Laboratory Manual, Cold Spring Harbor Laboratory. New York, 1989). The cDNA libraries are also commercially available. For example, Clontech Ltd. has various cDNA libraries. When PCR is further used, even an extremely small amount of expression products can be cloned.

Methods can be used for screening for the polynucleotide of the invention from cDNA library. These methods include, but are not limited to, (1) DNA—DNA or DNA-RNA hybridization; (2) the appearance or loss of the function of the marker-gene; (3) the determination of the level of A steroid dehydrogenase 34 transcripts; (4) the determination of protein product of gene expression by immunology methods or the biological activity assays. The above methods can be used alone or in combination.

In method (1), the probe used in the hybridization could be homologous to any portion of polynucleotide of invention. The length of probe is typically at least 10 nucleocides, preferably at least 30 nucleocides, more preferably at least 50 nucleocides, and most preferably at least 100 nucleotides. Furthermore, the length of the probe is usually less than 2000 nucleotides, preferably less than 1000 nucleotides. The probe usually is the DNA sequence chemically synthesized on the basis of the sequence information. Of course, the gene of the invention itself or its fragment can be used as a probe. The labels for DNA probe include, e.g., radioactive isotopes, fluoresceins or enzymes such as alkaline phosphatase.

In method (4), the detection of the protein products expressed by A steroid dehydrogenase 34 gene can be carried out by immunology methods, such as Western blotting, radioimmunoassay, and ELISA.

The method of amplification of DNA/RNA by PCR (Saiki, et al. Science 1985; 230:1350–1354) is preferably used to obtain the polynucleotide of the invention. Especially when it is difficult to obtain the full-length cDNA, the method of RACE (RACE—cDNA terminate rapid amplification) is preferably used. The primers used in PCR can be selected according to the polynucleotide sequence information of the invention disclosed herein, and can be synthesized by conventional methods. The amplified DNA/RNA fragments can be isolated and purified by conventional methods such as gel electrophoresis.

Sequencing of polynucleotide sequence of the gene of the invention or its various DNA fragments can be carried out by the conventional dideoxy sequencing method (Sanger et al. PNAS, 1977, 74: 5463–5467). Sequencing of polynucleotide sequence can also be carried out using the commercially available sequencing kits. In order to obtain the full-length cDNA sequence, it is necessary to repeat the sequencing process. Sometimes, it is needed to sequence the cDNA of several clones to obtain the full-length cDNA sequence.

The invention further relates to a vector comprising the polynucleotide of the invention, a gentically engineered host cell transformed with the vector of the invention or directly with the sequence encoding a steroid dehydrogenase 34, and a method for producing the polypeptide of the invention by recombinant techniques.

In the present invention, the polynucleotide sequences encoding a steroid dehydrogenase 34 may be inserted into a vector to form a recombinant vector containing the polynucleotide of the invention. The term "vector" refers to a bacterial plasmid, bacteriophage, yeast plasmid, plant virus or mammalian virus such as adenovirus, retrovirus or any other vehicle known in the art. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. Any plasmid or vector can be used to construct the recombinant expression vector as long as it can replicate and is stable in the host. One important feature of an expression vector is that the expression vector typically contains an origin of replication, a promoter, a marker gene as well as the translation regulatory components.

Methods known in the art can be used to construct an expression vector containing the DNA sequence of A steroid dehydrogenase 34 and appropriate transcription/translation regulatory components. These methods include in vitro recombinant DNA technique, DNA synthesis technique, in vivo recombinant technique and so on (Sambroook, et al. Molecular Cloning, a Laboratory Manual, cold Spring Harbor Laboratory. New York, 1989). The DNA sequence is operatively linked to a proper promoter in an expression vector to direct the synthesis of mRNA. Exemplary promoters are lac or trp promoter of $E.\ coli$; $P_L$ promoter of $\lambda$ phage; eukaryotic promoters including CMV immediate early promoter, HSV thymidine kinase promoter, early and late SV40 promoter, LTRs of retrovirus and other known promoters which control gene expression in the prokaryotic cells, eukaryotic cells or virus. The expression vector may further comprise a ribosome binding site for initiating the translation, transcription terminator and the like. Transcription in higher eukaryotes is increased by inserting an enhancer sequence into the vector. Enhancers are cis-acting elements of DNA, expression usually about from 10 to 300 bp in length that act on a promoter to increase gene transcription level. Examples include the SV40 enhancer on the late side of the replication origin 100 to 270 bp, the polyoma enhancer on the late side of the replication origin, and adenovirus enhancers.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for $E.\ coli$.

The skilled in the art know clearly how to select appropriate vectors, transcriptional regulatory elements, e.g., promoters, enhancers, and selective marker gene.

According to the invention, polynucleotide encoding a steroid dehydrogenase 34 or recombinant vector containing said polynucleotide can be transformed or transfected into host cells to construct genetically engineered host cells containing said polynucleotide or said recombinant vector. The term "host cell" means prokaryote, such as bacteria; or primary eukaryote, such as yeast; or higher eukaryotic, such as mammalian cells. Representative examples are bacterial cells, such as *E. coli, Streptomyces, Salmonella typhimurium*; fungal cells, such as yeast; plant cells; insect cells such as *Drosophila* S2 or Sf9; animal cells such as CHO, COS or Bowes melanoma.

Transformation of a host cell with the DNA sequence of invention or a recombinant vector containing said DNA sequence may be carried out by conventional techniques as are well known to those skilled in the art. When the host is prokaryotic, such as *E. coli*, competent cells, which are capable of DNA uptake, can be prepared from cells harvested after exponential growth phase and subsequently treated by the $CaCl_2$ method using procedures well known in the art. Alternatively, $MgCl_2$ can be used. Transformation can also be carried out by electroporation, if desired. When the host is an eukaryote, transfection method as well as calcium phosphate co-precipitation method may be used. Conventional mechanical procedures such as micro-injection, electroporation, or liposome-mediated transfection may also be used.

The recombinant A steroid dehydrogenase 34 can be expressed or produced by the conventional recombinant DNA technology (Science, 1984; 224:1431), using the polynucleotide sequence of the invention. The steps generally include:

(1) transfecting or transforming the appropriate host cells with the polynucleotide (or variant) encoding human A steroid dehydrogenase 34 of the invention or the recombinant expression vector containing said polynucleotide;

(2) culturing the host cells in an appropriate medium; and (3) isolating or purifying the protein from the medium or cells.

In Step (2) above, depending on the host cells used, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In Step (3), the recombinant polypeptide may be included in the cells, or expressed on the cell membrane, or secreted out of the cell. If desired, physical, chemical and other properties can be utilized in various isolation methods to isolate and purify the recombinant protein. These methods are well-known to those skilled in the art and include, but are not limited to conventional renaturation treatment, treatment by a protein precipitant (such as salt precipitation), centrifugation, cell lysis by osmosis, sonication, supercentrifugation, molecular sieve chromatography or gel chromatography, adsorption chromatography, ion exchange chromatagraphy, HPLC, and any other liquid chromatagraphy, and a combination thereof.

17beta-hydroxy-steroid dehydrogenase is an enzyme which catalyzes specifically the dehydrogenation/reduction of 17beta-hydroxy-steroid hormones or prohormones. The common function of this hydroxy-steroid dehydrogenase family is to catalyze metabolism of steroid. Its product as a hormone binds with the receptor more efficiently than the prohormone thereby effecting regulation functions. The product can also be used by other enzymes as a prohormone, thus continuing the pathway of steroid metabolism. Accordingly, abnormality in steroid dehydrogenase 34 gene and the expression product thereof may result in abnormality in metabolism of steroid hormones, especially dysbolism of the steroid hormones secreted by gonads and adrenal cortex, such as testosterone, estradiol, estriol, progesterone, cortisol and, aldosterone, thus causing diseases of dysbolism of such steroid hormones. These diseases include, but are not limited to:

Sexual dysbolism in the grown period: (1) Proiotia: idiopathic genuine proiotia, secondary gennuine proiotia such as proiotia caused by organic cerebropathy, multiple osteodystrophia fibrosa accompanied with proiotia syndrome, primary hypothyrea accompanied with proiotia, unilateral hypertrophy dwarf accompanied with proiotia syndrome, and genuine proiotia, pseudo-proiotia, incomplete proiotia, e.g., simple mammary tachygenesis, mammary feminism, simple pubisure anticipation and, isolated menarche caused by other reasons. (2) sexual hypoevolutism: hypogonadotrophic puberty and sexual hypoevolutism such as adiposogenital syndrome, hypopre, hypophysis obesity syndrome with low level of three hormanes, sex infantilism polydactylia syndrome, dysosmia and dysgenitalism syndrome, hypergonadotrophic puberty and sexual hypoevolutism, such as congenital hypoplasia of orchis, congenital ovirian agenesis, congenital orchis deletion syndrome and simple hypogonadism (3) defect of sexual differentiation: abnormality of isosexual differentiation such as Turner syndrome, abnormality of heterologous differentiation such as hermaphroditism and pseudohermaphroditism, e.g., male pseudohermaphroditism and female pseudohermaphroditism, (4) and other dysplasia of externalia.

Other diseases include endocrine and metabolism syndromes, hyperinterrenopathy such as Cushing syndrome, hyperaldosteronism, hyperinterrenopathy such as acute hypoadrenocortism and chronic hypoadrenocortism.

It is shown that 17beta-hydroxy-steroid dehydrogenase (type II), plays an important role in the carcinogenosis of mammary gland and ovary in human. Abnormality of the steroid dehydrogenase 34 gene of the invention and the expression product thereof may result in tumors of reproductive system in human. These tumors include, but are not limited to: mammary cancer, malignant ovarian tumor, benign ovarian tumor, oviduct cancer, cervix cancer, endometrial carcinoma, uterine choriocarcinoma, endometrial mesenchymoma, seminoma, tumour of orchic matrix cell, fibroadenoma of the breast prostatic cancer, orchic tumor choriocarcinoma and parorchis cancer.

It is shown that 17beta-hydroxy-steroid dehydrogenase (type IV) plays an important role in catalyzing the oxidation of bile acid precursor. Abnormality of steroid dehydrogenase 34 gene and the expression product thereof may induce dysbolism of bile acid. These diseases include, but are not limited to: biliary hepatocirrhosis (cholestatic hepatocirrhosis, cholangitic biliary hepatocirrhosis, primary biliary hepatocirrhosis), gall-stone, pigent hepatocirrhosis.

The polypeptide of the invention and its antagonists, agonists and inhibitors thereof can be directly used for the treatment of diseases, e.g., various diseases of dysbolism of such steroid hormones, such as dysbolism in the grown period, some endocrinopathy and metabolism syndrome, various tumours and cancers of human reproductive system, dysbolism of bile acid, etc.

The invention also provides methods for screening compounds so as to identify an agent which enhances a steroid dehydrogenase 34 activity (agonists) or decrease a steroid dehydrogenase 34 activity (antagonists). The agonists enhance the biological functions of a steroid dehydrogenase 34 such as inactivation of cell proliferation, while the antagonists prevent and cure the disorders associated with the excess cell proliferation, such as various cancers. For example, in the presence of an agent, the mammal cells or the membrane preparation expressing a steroid dehydrogenase 34 can be incubated with the labeled a steroid dehydrogenase 34 to determine the ability of the agent to enhance or repress the interaction.

Antagonists of a steroid dehydrogenase 34 include antibodies, compounds, receptor deletants and analogues. The antagonists of a steroid dehydrogenase 34 can bind to a steroid dehydrogenase 34 and eliminate or reduce its function, or inhibit the production of A steroid dehydrogenase 34, or bind to the active site of said polypeptide so that the polypeptide can not function biologically.

When screening for compounds as an antagonist, a steroid dehydrogenase 34 may be added into a biological assay. It can be determined whether the compound is an antagonist or not by determining its effect on the interaction between a steroid dehydrogenase 34 and its receptor. Using the same method as that for screening compounds, receptor deletants and analogues acting as antagonists can be selected. Polypeptide molecules capable of binding to a steroid dehydrogenase 34 can be obtained by screening a polypeptide library comprising the various combinations of amino acids bound onto a solid matrix. Usually, a steroid dehydrogenase 34 is labeled in the screening.

The invention further provides a method for producing antibodies using the polypeptide, and its fragment, derivative, analogue or cells as an antigen. These antibodies may be polyclonal or monoclonal antibodies. The invention also provides antibodies against epitopes of a steroid dehydrogenase 34. These antibodies include, but are not limited to, polyclonal antibody, monoclonal antibody, chimeric antibody, single-chain antibody, Fab fragment and the fragments produced by a Fab expression library.

Polyclonal antibodies can be prepared by immunizing animals, such as rabbit, mouse, and rat, with a steroid dehydrogenase 34. Various adjuvants, including but are not limited to Freund's adjuvant, can be used to enhance the immunization. The techniques for producing a steroid dehydrogenase 34 monoclonal antibodies include, but are not limited to, the hybridoma technique (Kohler and Milstein. Nature, 1975, 256:495–497), the trioma technique, the human B-cell hybridoma technique, the EBV-hybridoma technique and so on. A chimeric antibody comprising a constant region of human origin and a variable region of non-human origin can be produced using methods well-known in the art (Morrison et al, PNAS, 1985, 81:6851). Furthermore, techniques for producing a single-chain antibody (U.S. Pat. No. 4,946,778) are also useful for preparing single-chain antibodies against a steroid dehydrogenase 34.

The antibody against a steroid dehydrogenase 34 can be used in immunohistochemical method to detect the presence of a steroid dehydrogenase 34 in a biopsy specimen.

The monoclonal antibody specific to a steroid dehydrogenase 34 can be labeled by radioactive isotopes, and injected into human body to trace the location and distribution of a steroid dehydrogenase 34. This radioactively labeled antibody can be used in the non-wounding diagnostic method for determination of tumor location and metastasis.

Antibodies can also be designed as an immunotoxin targeting a particular site in the body. For example, a monoclonal antibody having high affinity to a steroid dehydrogenase 34 can be covalently bound to bacterial or plant toxins, such as diphtheria toxin, ricin, ormosine. One common method is to challenge the amino group on the antibody with sulfydryl cross-linking agents, such as SPDP, and bind the toxin onto the antibody by interchanging the disulfide bonds. This hybrid antibody can be used to kill a steroid dehydrogenase 34-positive cells.

The antibody of the invention is useful for the therapy or the prophylaxis of disorders related to the a steroid dehydrogenase 34. The appropriate amount of antibody can be administrated to stimulate or block the production or activity of a steroid dehydrogenase 34.

The invention further provides diagnostic assays for quantitative and in situ measurement of a steroid dehydrogenase 34 level. These assays are well known in the art and include FISH assay and radioimmunoassay. The level of a steroid dehydrogenase 34 detected in the assay can be used to illustrate the importance of a steroid dehydrogenase 34 in diseases and to determine the diseases associated with a steroid dehydrogenase 34.

The polypeptide of the invention is useful in the analysis of polypeptide profile. For example, the polypeptide can be specifically cut by physical, chemical, or enzymatic means, and then analyzed by one, two or three dimensional gel electrophoresis, preferably by spectrometry.

A steroid dehydrogenase 34 polynucleotides also have many therapeutic applications. Gene therapy technology can be used in the therapy of abnormal cell proliferation, development or metabolism, which are caused by the loss of A steroid dehydrogenase 34 expression or the abnormal or non-active expression of A steroid dehydrogenase 34. Recombinant gene therapy vectors, such as virus vectors, can be designed to express mutated A steroid dehydrogenase 34 so as to inhibit the activity of endogenous A steroid dehydrogenase 34. For example, one form of the mutated A steroid dehydrogenase 34 is a truncated A steroid dehydrogenase 34 whose signal transduction domain is deleted. Therefore, this mutated A steroid dehydrogenase 34 can bind the downstream substrate without the activity of signal transduction. Thus, the recombinant gene therapy vectors can be used to cure diseases caused by abnormal expression or activity of A steroid dehydrogenase 34. The expression vectors derived from a virus, such as retrovirus, adenovirus, adeno-associated virus, herpes simplex virus, parvovirus, and so on, can be used to introduce the A steroid dehydrogenase 34 gene into the cells. The methods for constructing a recombinant virus vector harboring A steroid dehydrogenase 34 gene are described in the literature (Sambrook, et al. supra). In addition, the recombinant A steroid dehydrogenase 34 gene can be packed into liposome and then transferred into the cells.

The methods for introducing the polynucleotides into tissues or cells include directly injecting the polynucleotides into tissue in the body; or introducing the polynucleotides into cells in vitro with vectors, such as virus, phage, or plasmid, etc, and then transplanting the cells into the body.

Also included in the invention are ribozyme and the oligonucleotides, including antisense RNA and DNA, which inhibit the translation of A steroid dehydrogenase 34 mRNA. Ribozyme is an enzyme-like RNA molecule capable of specifically cutting certain RNA. The mechanism is nucleic acid endo-cleavage following specific hybridization of ribozyme molecule and the complementary target RNA. Antisense RNA and DNA as well as ribozyme can be prepared by using any conventional techniques for RNA and DNA synthesis, e.g., the widely used solid phase phosphite chemical method for oligonucleotide synthesis. Antisense RNA molecule can be obtained by the in vivo or in vitro transcription of the DNA sequence encoding said RNA, wherein said DNA sequence is integrated into the vector and downstream of the RNA polymerase promoter. In order to increase its stability, a nucleic acid molecule can be modified in many manners, e.g., increasing the length of two the flanking sequences, replacing the phosphodiester bond with the phosphothioester bond in the oligonucleotide.

The polynucleotide encoding a steroid dehydrogenase 34 can be used in the diagnosis of a steroid dehydrogenase 34 related diseases. The polynucleotide encoding a steroid dehydrogenase 34 can be used to detect whether a steroid dehydrogenase 34 is expressed or not, and whether the expression of a steroid dehydrogenase 34 is normal or abnormal in the case of diseases. For example, a steroid dehydrogenase 34 DNA sequences can be used in the hybridization with biopsy samples to determine the expression of a steroid dehydrogenase 34. The hybridization methods include Southern blotting, Northern blotting and in situ blotting, etc., which are well-known and established techniques. The corresponding kits are commercially available. A part of or all of the polynucleotides of the invention can be used as probe and fixed on a microarray or DNA chip for the analysis of the differential expression of genes in tissues and for the diagnosis of genes. The a steroid dehydrogenase 34 specific primers can be used in RNA-polymerase chain reaction and in vitro amplification to detect the transcripts of A steroid dehydrogenase 34.

Further, detection of mutations in steroid dehydrogenase 34 gene is useful for the diagnosis of a steroid dehydrogenase 34-related diseases. Mutations of a steroid dehydrogenase 34 include site mutation, translocation, deletion, rearrangement and any other mutations compared with the wild-type A steroid dehydrogenase 34 DNA sequence. The conventional methods, such as Southern blotting, DNA sequencing, PCR and in situ blotting, can be used to detect a mutation. Moreover, mutations sometimes affects the expression of protein. Therefore, Northern blotting and Western blotting can be used to indirectly determine whether the gene is mutated or not.

Sequences of the present invention are also valuable for chromosome identification. The sequence is specifically targeted to and can hybridize with a particular location on an individual human chromosome. There is a current need for identifying particular sites of gene on the chromosome. Few chromosome marking reagents based on actual sequence data (repeat polymorphism) are presently available for marking chromosomal location. The mapping of DNA to chromosomes according to the present invention is an important first step in correlating those sequences with genes associated with disease.

Briefly, sequences can be mapped to chromosomes by preparing PCR primers (preferably 15–35 bp) from the cDNA. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the oligonucleotide primers of the invention, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis.

Next, it is necessary to determine the differences in the cDNA or genomic sequence between affected and unaffected individuals. If a mutation is observed in some or all of the affected individuals but not in any normal individuals, then the mutation is likely to be the cause of the disease. Comparison of affected and unaffected individuals generally involves first looking for structural alterations in the chromosomes, such as deletions or translocations, that are visible from chromosome level, or detectable using PCR based on that DNA sequence. With current resolution of physical mapping and genetic mapping techniques, a cDNA precisely localized to a chromosomal region associated with the disease could be one of 50 to 500 potential causative genes. (This assumes 1 megabase mapping resolution and one gene per 20 kb).

According to the invention, the polypeptides, polynucleotides and its mimetics, agonists, antagonists and inhibitors may be employed in combination with a suitable pharmaceutical carrier. Such a carrier includes but is not limited to water, glucose, ethanol, salt, buffer, glycerol, and combinations thereof. Such compositions comprise a safe and effective amount of the polypeptide or antagonist, as well as a pharmaceutically acceptable carrier or excipient with no influence on the effect of the drug. These compositions can be used as drugs in disease treatment.

The invention also provides a pharmaceutical pack or kit comprising one or more containers filled with one or more of the ingredients of the pharmaceutical compositions of the invention. With such container(s) there may be a notice written by a governmental agency, that regulates the manufacture, use or sale of pharmaceuticals or biological products, the notice reflects government's approval for the manufacture, use or sale for human administration. In addition, the polypeptides of the invention may be employed in conjunction with other therapeutic compounds.

The pharmaceutical compositions may be administered in a convenient manner, such as through topical, intravenous, intraperitoneal, intramuscular, subcutaneous, intranasal or intradermal routes. A steroid dehydrogenase 34 is administered in an amount, which is effective for treating and/or prophylaxis of the specific indication. The amount of A steroid dehydrogenase 34 administrated on patient will depend upon various factors, such as delivery methods, the subject health, the judgment of the skilled clinician.

EXAMPLE

The invention is further illustrated by the following examples. It is appreciated that these examples are only intended to illustrate the invention, not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

Example 1

Cloning of Steroid Dehydrogenase 34 Gene

The total RNA from human embryo brain was extracted by one-step method with guanidinium isocyanate/phenol/chloroform. The poly(A) mRNA was isolated from the total RNA with Quik mRNA Isolation Kit (Qiegene). cDNA was prepared by reverse transcription with 2 ug poly(A) mRNA. The cDNA fragments were inserted into the polyclonal site of pBSK(+) vector (Clontech) using Smart cDNA cloning kit (Clontech) and then transformed into DH5α to form the cDNA library. The 5'- and 3'-ends of all clones were sequenced with Dye terminate cycle reaction sequencing kit (Perkin-Elmer) and ABI 377 Automatic Sequencer (Perkin-Elmer). The sequenced cDNA were compared with the public database of DNA sequences (Genebank) and the DNA sequence of one clone 0028b11 was found to be a novel DNA sequence. The inserted cDNA sequence of clone 0028b11 was dual-directionally sequenced with a serial of synthesized primers. It was indicated that the full length cDNA contained in clone 0028b11 was 1416 bp (SEQ ID NO: 1) with a 9029 bp ORF located in positions 112–1041 which encoded a novel protein (SEQ ID NO: 2). This clone was named pBS-0028b11 and the encoded protein was named steroid dehydrogenase 34.

Example 2

Homology Search of cDNA Clone

The homology research of the DNA sequence and its protein sequence of A steroid dehydrogenase 34 of the invention were performed by Blast (Basic local Alignment search tool) in the databases such as Genbank, Swissport, etc. The most homologous gene to a steroid dehydrogenase 34 of the invention is known 17beta-hydroxy-steroid dehydrogenas, (type III). The Genbank accession number of its encoded protein is U05659. The alignment result of the protein was shown in FIG. 1. Two proteins are highly homologous with an identity of 46% and a similarity of 39%.

Example 3

Cloning Steroid Dehydrogenase 34 Gene by RT-PCR

The template was total RNA extracted from embryo brain. The reverse transcription was carried out with oligo-dT primer to produce cDNA. After cDNA purified with Qiagen Kit, PCR was carried out with the following primers:

Primer1: 5'-GGAGCCACATACTGCTGACGGC-3' (SEQ ID NO: 3)

Primer2: 5'-ATTGGAAAAGAATTCACTATAG-3' (SEQ ID NO: 4)

Primer1 is the forward sequence started from position 1 of 5' end of SEQ ID NO: 1.

Primer2 is the reverse sequence of the 3' end of SEQ ID NO: 1.

The amplification condition was a 50 ul reaction system containing 50 mmol/L KCl, 10 mmol/L Tris-Cl (pH8.5), 1.5 mmol/L MgCl$_2$, 200 umol/L dNTP, 10 pmol of each primer, 1 U Taq DNA polymerase (Clontech). The reaction on a PE 9600 DNA amplifier subjected to 94° C. 30 sec, 55° C. 30 sec, and 72° C. 2 min for 25 cycles. The β-actin was used as a positive control, and a blank template, as a negative control in RT-PCR. The amplified products were purified with QIAGEN kit, and linked with pCR vector (Invitrogen) using TA Cloning Kit. The DNA sequencing results show that the DNA sequence of PCR products was identical to nucleotides 1–1416 of SEQ ID NO: 1.

Example 4

Northern Blotting of Expression Steroid Dehydrogenase 34 Gene Expression Product The total RNA was extracted by one-step method (Anal. Biochem 1987, 162, 156–159) with guanidinium isocyanate-phenol-chloroform. That is, homogenate the organize using 4M guanidinium isocyanate-25 mM sodium citrate, add 1 volume phenol and ⅕ volume chloroform-isoamyl alcohol (49:1), centrifuge after mixing. Take out the water phase, add 0.8 volume isopropyl alcohol, then centrifuge the mixture. Wash the RNA precipitation using 70% ethanol, then dry, then dissolve it in the water. 20 μg RNA was electrophoresed on the 1.2% agarose gel containing 20 mM 3-(N-morpholino) propane sulfonic acid (pH 7.0)-5 mM sodium acetate-imM EDTA-2.2M formaldehyde. Then transfer it to a nitrocellulose filter. Prepare the $^{32}$P-labelled DNA probe with α-$^{32}$P dATP by random primer method. The used DNA probe is the coding sequence (112 bp–1041 bp) of A steroid dehydrogenase 34 amplified by PCR indicated in FIG. 1. The nitrocellulose filter with the transferred RNA was hybridized with the $^{32}$P-labelled DNA probe (2×10$^6$ cpm/ml) overnight in a buffer containing 50% formamide-25 mM KH$_2$PO$_4$(Ph7.4)-5× Denhardt's solution and 200 μg/ml salmine. Then wash the filter in the 1×SSC-0.1% SDS, at 55° C., for 30 min. Then analyze and quantitative determinate using Phosphor Imager.

Example 5

In vitro Expression, Isolation and Purification of Recombinant Steroid Dehydrogenase 34

A pair of primers for specific amplification was designed based on SEQ ID NO: 1 and the encoding region in FIG. 1, the sequences are as follows:

Primer3: 5'-CCCCATATGATGGAAGCTCTAGCTTTG-GTTGG-3'(SEQ ID NO: 5)

Primer4: 5'-CCCGGATCCTCAGGCTGTGCAG-GATAAGGC-3'(SEQ ID NO: 6)

These two primers contain NcoI and BamHI cleavage site on the 5' end respectively, and following the site is the encoding sequences of the 5' and 3' end of the desired gene. NcoI and BamHI cleavage sites were corresponding to the selective cleavage sites on the expression vector pET-28b(+) (Novagen, Cat. No. 69865.3). PCR amplification was performed with the plasmid 0028b11 containing the full-length target gene as a template. The PCR reaction was subject to a 50 ul system containing 10 pg pBS-0028b11 plasmid, 10 pmol of Primer-3 and 10 pmol of Primer-4, 1 ul of Advantage polymerase Mix (Clontech). The parameters of PCR were 94° C. 20 sec, 60° C. 30 sec, and 68° C. 2 min for 25 cycles. After digesting the amplification products and the plasmid pET-28(+) by NcoI and BamHI, the large fragments were recovered and linked together with T4 ligase. The linkage product was transformed into *E. coli* DH5α with the calcium chloride method. After cultured overnight on a LB plate containing a final concentration of 30 ug/ml kanamycin, the positive clones were selected out using colony PCR and then sequenced. The positive clone pET-0028b11 with the correct sequence was selected out and the recombinant plasmid thereof was transformed into BL21(DE3)plySs (Novagen) using the calcium chloride method. In a LB liquid medium containing a final concentration of 30 ug/ml of kanamycin, the host bacteria BL21(Pet-0028b11) were cultured at 37° C. to the exponential growth phase, then IPTG were added with the final concentration of 1 mmol/L, the cells were cultured for another 5 hours, and then centrifuged to harvest the bacteria. After the bacteria were sonicated, the supernatant was collected by centrifugation. Then the purified desired protein—a steroid dehydrogenase 34 was obtained by being isolated on a His.Bind Quick Cartridge (Novagen) affinity column with binding 6His-Tag. SDS-PAGE showed a single band at 34.0 kDa (FIG. 2). The said band was transferred onto the PVDF membrane and the N terminal amino acid was sequenced by Edams Hydrolysis, which shows that the first 15 amino acids on N-terminus were identical to those in SEQ ID NO: 2.

Example 6

Preparation of Antibody Against Steroid Dehydrogenase 34

The following specific A steroid dehydrogenase 34 polypeptide was synthesized by a polypeptide synthesizer (PE-ABI): NH2-Met-Glu-Ala-Leu-Ala-Leu-Val-Gly-Ala-Trp-Tyr-Thr-Ala-Arg-Lys-COOH(SEQ ID NO:7). The polypeptide was conjugated with hemocyanin and bovine serum albumin (BSA) respectively to form two composites (See Avrameas. et al., Immunochemistry, 1969; 6:43). 4 mg of hemocyanin-polypeptide composite was used to immunize rabbit together with Freund's complete adjuvant. The rabbit was re-immunized with the hemocyanin-polypeptide composite and Freund's incomplete 15 days later. The titer of antibody in the rabbit sera was determined with a titration plate coated with 15 ug/ml BSA-polypeptide composite by ELISA. The total IgG was isolated from the sera of an antibody positive rabbit with Protein A-Sepharose. The polypeptide was bound to Sepharose 4B column activated by cyanogen bromide. The antibodies against the polypeptide were isolated from the total IgG by affinity chromatography. The immunoprecipitation approved that the purified antibodies could specifically bind to A steroid dehydrogenase 34.

What is claimed is:

1. An isolated polynucleotide selected from the group consisting of:
   (a) a polynucleotide encoding a polypeptide that has a steroid dehydrogenase 34 activity and is at least 95% identical to SEQ ID NO: 2; or
   (b) a polynucleotide complementary to polynucleotide (a).

2. The polynucleotide of claim 1 wherein the polynucleotide encodes an amino acid sequence of SEQ ID NO:2.

3. The polynucleotide of claim 1 wherein the sequence of said polynucleotide comprises nucleotides 112–1041 of SEQ ID NO:1.

4. The polynucleotide of claim 1 wherein the sequence of said polynucleotide comprises nucleotides 1–1416 of SEQ ID NO:1.

5. A recombinant vector comprising the polynucleotide of claim 1, and a suitable regulatory element.

6. A genetically engineered host cell comprising the polynucleotide of claim 1.

7. A method for producing a polypeptide having an activity of a steroid dehydrogenase 34 which comprises the steps of:
   (a) culturing the engineered host cell of claim 6 under conditions suitable for the expression of a steroid dehydrogenase 34; and
   (b) isolating a polypeptides having the activity of a steroid dehydrogenase 34 from the culture.

8. A pharmaceutical composition comprising the polynucleotide according to claim 1, and a pharmaceutically acceptable carrier.

* * * * *

SEQUENCE LISTING

<160> NUMBER OF SEQ ID NOS: 8

<210> SEQ ID NO 1
<211> LENGTH: 1416
<212> TYPE: DNA
<213> ORGANISM: Homo sapiens
<220> FEATURE:
<221> NAME/KEY: CDS
<222> LOCATION: (112)..(1041)

<400> SEQUENCE: 1

```
ggagccacat actgctgacg gcccagaact ggcagagaga aggttgccgt ggctgctgtt        60
gacagtttct acctcttgta cagggaaatc gccaggtctt gcaattgcta t atg gaa       117
                                                         Met Glu
                                                           1 gct cta gct ttg gtt gga gcc tgg tat acg gcc aga aaa agc atc act        165
Ala Leu Ala Leu Val Gly Ala Trp Tyr Thr Ala Arg Lys Ser Ile Thr
        5                  10                  15 gtc atc tgt gac ttt tac agc ctg atc agg ctg cat ttt atc ccc cgc        213
Val Ile Cys Asp Phe Tyr Ser Leu Ile Arg Leu His Phe Ile Pro Arg
     20                  25                  30 ctg ggg agc aga gca gac ttg atc aag cag tat gga aga tgg gcc gtt        261
Leu Gly Ser Arg Ala Asp Leu Ile Lys Gln Tyr Gly Arg Trp Ala Val
 35                  40                  45                  50 gtc agc ggt gca aca gat ggg att gga aaa gcc tac gct gaa gag tta        309
Val Ser Gly Ala Thr Asp Gly Ile Gly Lys Ala Tyr Ala Glu Glu Leu
             55                  60                  65 gca agc cga ggt ctc aat ata atc ctg att agt cgg aac gag gag aag        357
Ala Ser Arg Gly Leu Asn Ile Ile Leu Ile Ser Arg Asn Glu Glu Lys
         70                  75                  80 ttg cag gtt gtt gct aaa gac ata gcc gac acg tac aaa gtg gaa act        405
Leu Gln Val Val Ala Lys Asp Ile Ala Asp Thr Tyr Lys Val Glu Thr
     85                  90                  95 gat att ata gtt gcg gac ttc agc agc ggt cgt gag atc tac ctt cca        453
Asp Ile Ile Val Ala Asp Phe Ser Ser Gly Arg Glu Ile Tyr Leu Pro
    100                 105                 110 att cga gaa gcc ctg aag gac aaa gac gtt ggc atc ttg gta aat aac        501
Ile Arg Glu Ala Leu Lys Asp Lys Asp Val Gly Ile Leu Val Asn Asn
115                 120                 125                 130
```

```
gtg ggt gtg ttt tat ccc tac ccg cag tat ttc act cag ctg tcc gag       549
Val Gly Val Phe Tyr Pro Tyr Pro Gln Tyr Phe Thr Gln Leu Ser Glu
                135                 140                 145 gac aag ctc tgg gac atc ata aat gtg aac att gcc gcc gct agt ttg       597
Asp Lys Leu Trp Asp Ile Ile Asn Val Asn Ile Ala Ala Ala Ser Leu
            150                 155                 160 atg gtc cat gtt gtg tta ccg gga atg gtg gag aga aag aaa ggt gcc       645
Met Val His Val Val Leu Pro Gly Met Val Glu Arg Lys Lys Gly Ala
        165                 170                 175 atc gtc acg atc tct tct ggc tcc tgc tgc aaa ccc act cct cag ctg       693
Ile Val Thr Ile Ser Ser Gly Ser Cys Cys Lys Pro Thr Pro Gln Leu
    180                 185                 190 gct gca ttt tct gct tct aag gct tat tta gac cac ttc agc aga gcc       741
Ala Ala Phe Ser Ala Ser Lys Ala Tyr Leu Asp His Phe Ser Arg Ala
195                 200                 205                 210 ttg caa tat gaa tat gcc tct aaa gga atc ttt gta cag agt cta atc       789
Leu Gln Tyr Glu Tyr Ala Ser Lys Gly Ile Phe Val Gln Ser Leu Ile
                215                 220                 225 cct ttc tat gta gcc acc agc atg aca gca ccc agc aac ttt ctg cac       837
Pro Phe Tyr Val Ala Thr Ser Met Thr Ala Pro Ser Asn Phe Leu His
            230                 235                 240 agg tgc tcg tgg ttg gtg cct tcg cca aaa gtc tat gca cat cat gct       885
Arg Cys Ser Trp Leu Val Pro Ser Pro Lys Val Tyr Ala His His Ala
        245                 250                 255 gtt tct act ctt ggg att tcc aaa agg acc aca gga tat tgg tcc cat       933
Val Ser Thr Leu Gly Ile Ser Lys Arg Thr Thr Gly Tyr Trp Ser His
    260                 265                 270 tct att cag ttt ctt ttt gca cag tat atg cct gaa tgg ctc tgg gtg       981
Ser Ile Gln Phe Leu Phe Ala Gln Tyr Met Pro Glu Trp Leu Trp Val
275                 280                 285                 290 tgg gga gca aat att ctc aac cgt tca cta cgt aag gaa gcc tta tcc      1029
Trp Gly Ala Asn Ile Leu Asn Arg Ser Leu Arg Lys Glu Ala Leu Ser
                295                 300                 305 tgc aca gcc tga gtctggatgg ccacttgaga agttttgcca actcctggga          1081
Cys Thr Ala
acctcgatat tctgacattt ggaaaaacac atttaattta tctcctgtgt ttcattgctg    1141
attattcagc atactgttga ttcgtcattt gcaaaacaca cataataccg tcagagtgct    1201
gtgaaaaacc ttaagggtgt gtggatggca caggatcaat aatgcctgag gctgattgac    1261
gacatctaca tttcagtgct ttttccctaa gcttcgtctt ctcgcagccg tagtcgacgc    1321
ttaattaagc gaattcgata tcaagcttat cgataccgtc gacctcgagg ggggcccgg    1381 tacccaattc gccctatagt gaattctttt ccaat                              1416

<210> SEQ ID NO 2
<211> LENGTH: 309
<212> TYPE: PRT
<213> ORGANISM: Homo sapiens

<400> SEQUENCE: 2

Met Glu Ala Leu Ala Leu Val Gly Ala Trp Tyr Thr Ala Arg Lys Ser
1               5                   10                  15

Ile Thr Val Ile Cys Asp Phe Tyr Ser Leu Ile Arg Leu His Phe Ile
            20                  25                  30

Pro Arg Leu Gly Ser Arg Ala Asp Leu Ile Lys Gln Tyr Gly Arg Trp
        35                  40                  45

Ala Val Val Ser Gly Ala Thr Asp Gly Ile Gly Lys Ala Tyr Ala Glu
    50                  55                  60
```

```
Glu Leu Ala Ser Arg Gly Leu Asn Ile Ile Leu Ile Ser Arg Asn Glu
 65                  70                  75                  80

Glu Lys Leu Gln Val Val Ala Lys Asp Ile Ala Asp Thr Tyr Lys Val
                 85                  90                  95

Glu Thr Asp Ile Ile Val Ala Asp Phe Ser Ser Gly Arg Glu Ile Tyr
            100                 105                 110

Leu Pro Ile Arg Glu Ala Leu Lys Asp Lys Asp Val Gly Ile Leu Val
        115                 120                 125

Asn Asn Val Gly Val Phe Tyr Pro Tyr Pro Gln Tyr Phe Thr Gln Leu
130                 135                 140

Ser Glu Asp Lys Leu Trp Asp Ile Ile Asn Val Asn Ile Ala Ala Ala
145                 150                 155                 160

Ser Leu Met Val His Val Val Leu Pro Gly Met Val Glu Arg Lys Lys
                165                 170                 175

Gly Ala Ile Val Thr Ile Ser Ser Gly Ser Cys Cys Lys Pro Thr Pro
            180                 185                 190

Gln Leu Ala Ala Phe Ser Ala Ser Lys Ala Tyr Leu Asp His Phe Ser
        195                 200                 205

Arg Ala Leu Gln Tyr Glu Tyr Ala Ser Lys Gly Ile Phe Val Gln Ser
    210                 215                 220

Leu Ile Pro Phe Tyr Val Ala Thr Ser Met Thr Ala Pro Ser Asn Phe
225                 230                 235                 240

Leu His Arg Cys Ser Trp Leu Val Pro Ser Pro Lys Val Tyr Ala His
                245                 250                 255

His Ala Val Ser Thr Leu Gly Ile Ser Lys Arg Thr Thr Gly Tyr Trp
            260                 265                 270

Ser His Ser Ile Gln Phe Leu Phe Ala Gln Tyr Met Pro Glu Trp Leu
        275                 280                 285

Trp Val Trp Gly Ala Asn Ile Leu Asn Arg Ser Leu Arg Lys Glu Ala
290                 295                 300

Leu Ser Cys Thr Ala
305

<210> SEQ ID NO 3
<211> LENGTH: 22
<212> TYPE: DNA
<213> ORGANISM: Artificial
<220> FEATURE:
<223> OTHER INFORMATION: oligonucleotide primer

<400> SEQUENCE: 3
ggagccacat actgctgacg gc                                         22

<210> SEQ ID NO 4
<211> LENGTH: 22
<212> TYPE: DNA
<213> ORGANISM: Artificial
<220> FEATURE:
<223> OTHER INFORMATION: oligonucleotide primer

<400> SEQUENCE: 4
attggaaaag aattcactat ag                                         22

<210> SEQ ID NO 5
<211> LENGTH: 32
<212> TYPE: DNA
<213> ORGANISM: Artificial
<220> FEATURE:
<223> OTHER INFORMATION: oligonucleotide primer
```

-continued

```
<400> SEQUENCE: 5
ccccatatga tggaagctct agctttggtt gg                                    32

<210> SEQ ID NO 6
<211> LENGTH: 30
<212> TYPE: DNA
<213> ORGANISM: Artificial
<220> FEATURE:
<223> OTHER INFORMATION: oligonucleotide primer

<400> SEQUENCE: 6
cccggatcct caggctgtgc aggataaggc                                       30

<210> SEQ ID NO 7
<211> LENGTH: 15
<212> TYPE: PRT
<213> ORGANISM: Artificial
<220> FEATURE:
<223> OTHER INFORMATION: partial sequence of SEQ ID NO: 2

<400> SEQUENCE: 7

Met Glu Ala Leu Ala Leu Val Gly Ala Trp Tyr Thr Ala Arg Lys
1               5                   10                  15

<210> SEQ ID NO 8
<211> LENGTH: 240
<212> TYPE: PRT
<213> ORGANISM: Homo sapiens

<400> SEQUENCE: 8

Ala Val Ile Thr Gly Ala Gly Asp Gly Ile Gly Lys Ala Tyr Ser Phe
1               5                   10                  15

Glu Leu Ala Lys Arg Gly Leu Asn Val Val Leu Ile Ser Arg Thr Leu
                20                  25                  30

Glu Lys Leu Glu Ala Ile Ala Thr Glu Ile Glu Arg Thr Thr Gly Arg
            35                  40                  45

Ser Val Lys Ile Ile Gln Ala Asp Phe Thr Lys Asp Asp Ile Tyr Glu
        50                  55                  60

His Ile Lys Glu Lys Leu Ala Gly Leu Glu Ile Gly Ile Leu Val Asn
65                  70                  75                  80

Asn Val Gly Met Leu Pro Asn Leu Leu Pro Ser His Phe Leu Asn Ala
                85                  90                  95

Pro Asp Glu Ile Gln Ser Leu Ile His Cys Asn Ile Thr Ser Val Val
                100                 105                 110

Lys Met Thr Gln Leu Ile Leu Lys His Met Glu Ser Arg Gln Lys Gly
            115                 120                 125

Leu Ile Leu Asn Ile Ser Ser Gly Ile Ala Leu Phe Pro Trp Pro Leu
        130                 135                 140

Tyr Ser Met Tyr Ser Ala Ser Lys Ala Phe Val Cys Ala Phe Ser Lys
145                 150                 155                 160

Ala Leu Gln Glu Glu Tyr Lys Ala Lys Glu Val Ile Ile Gln Val Leu
                165                 170                 175

Thr Pro Tyr Ala Val Ser Thr Ala Met Thr Lys Tyr Leu Asn Thr Asn
                180                 185                 190

Val Ile Thr Lys Thr Ala Asp Glu Phe Val Lys Glu Ser Leu Asn Tyr
            195                 200                 205
```

```
-continued

Val Thr Ile Gly Gly Glu Thr Cys Gly Cys Leu Ala His Glu Ile Leu
    210                 215                 220

Ala Gly Phe Leu Ser Leu Ile Pro Ala Trp Ala Phe Tyr Ser Gly Ala
225                 230                 235                 240
```